United States Patent [19]

Teelmann

[11] Patent Number: 5,242,909
[45] Date of Patent: Sep. 7, 1993

[54] METHOD OF USING 4-(2-(P-((E)-2-(5,6,7,8-TETRAHYDRO-5,5,8,8-TETRAMETHYL-2-NAPHTHYL)PROPENYL)PHENOXY)ETHYL)MORPHOLINE WITH CYTOSTATICS

[75] Inventor: Kampe Teelmann, Basel, Switzerland

[73] Assignee: Hoffmann-La Roche Inc., Nutley, N.J.

[21] Appl. No.: 771,671

[22] Filed: Oct. 4, 1991

[30] Foreign Application Priority Data

Oct. 12, 1990 [CH] Switzerland .................. 3285/90

[51] Int. Cl.⁵ .................. A61K 31/66; A61K 31/535; A61K 49/00
[52] U.S. Cl. .................. 514/110; 514/237.8; 424/10
[58] Field of Search .................. 514/110, 237.8; 424/10

[56] References Cited

U.S. PATENT DOCUMENTS 4,940,707 7/1990 Klaus et al. .................. 514/237.8

FOREIGN PATENT DOCUMENTS 331983 9/1989 European Pat. Off. .

OTHER PUBLICATIONS

Carter et al., Chemotherapy of Cancer, 2nd Ed. John Wiley & Sons, N.Y., N.Y., pp. 67-68 (1981).

Primary Examiner—Jerome D. Goldberg
Attorney, Agent, or Firm—George M. Gould; George W. Johnston; William Krovatin

[57] ABSTRACT

The use of 4-[2-[p-[(E)-2-(5,6,7,8-tetrahydro-5,5,8,8-tetramethyl-2-naphthyl)-propenyl]phenoxy]ethyl]-morpholine, simultaneously, separately or sequentially in combination with a synergistically effective amount of cyclophosphamide in cancer prophylaxis or therapy for mammary tumors in mammals is described.

2 Claims, 14 Drawing Sheets

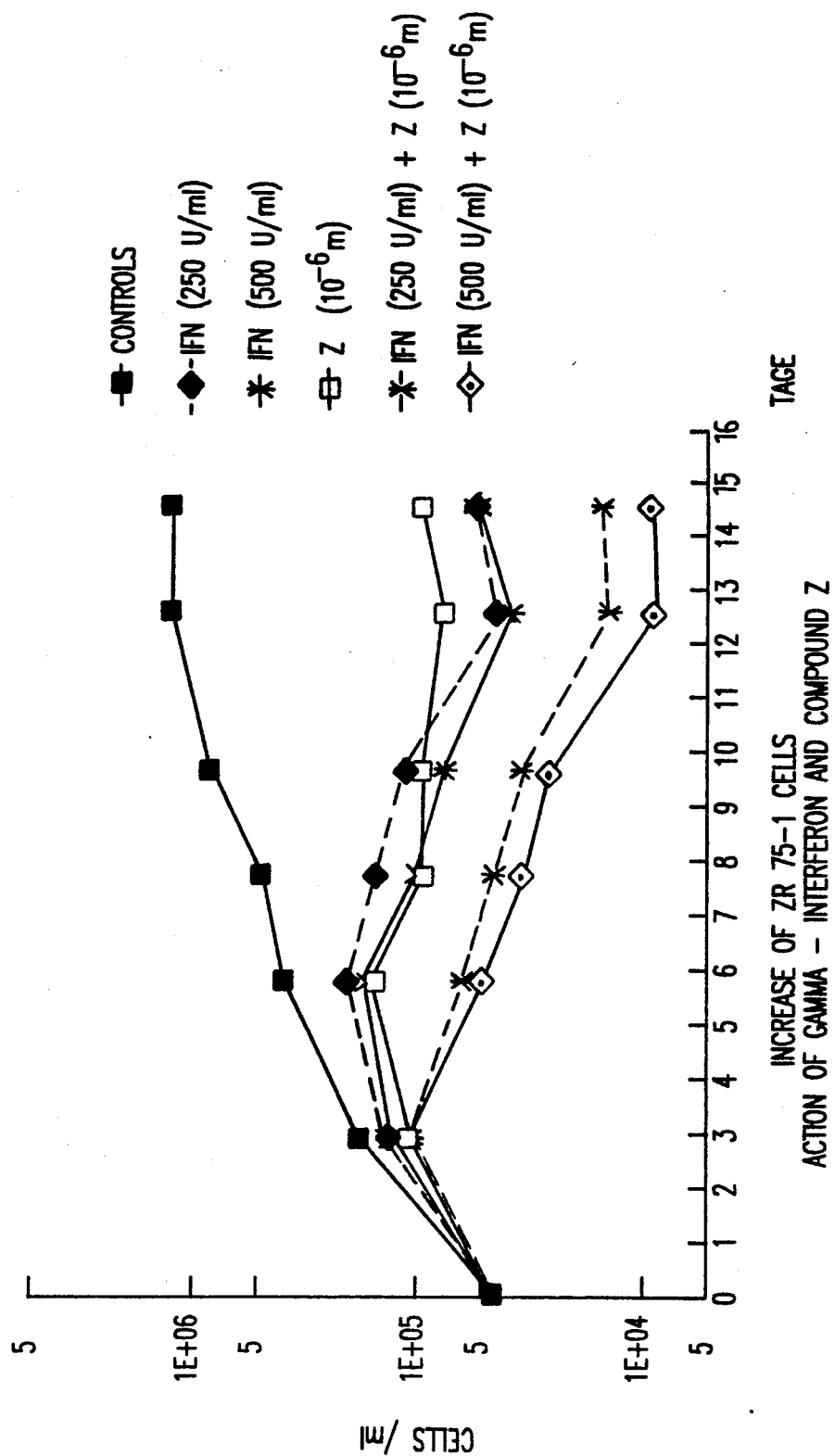

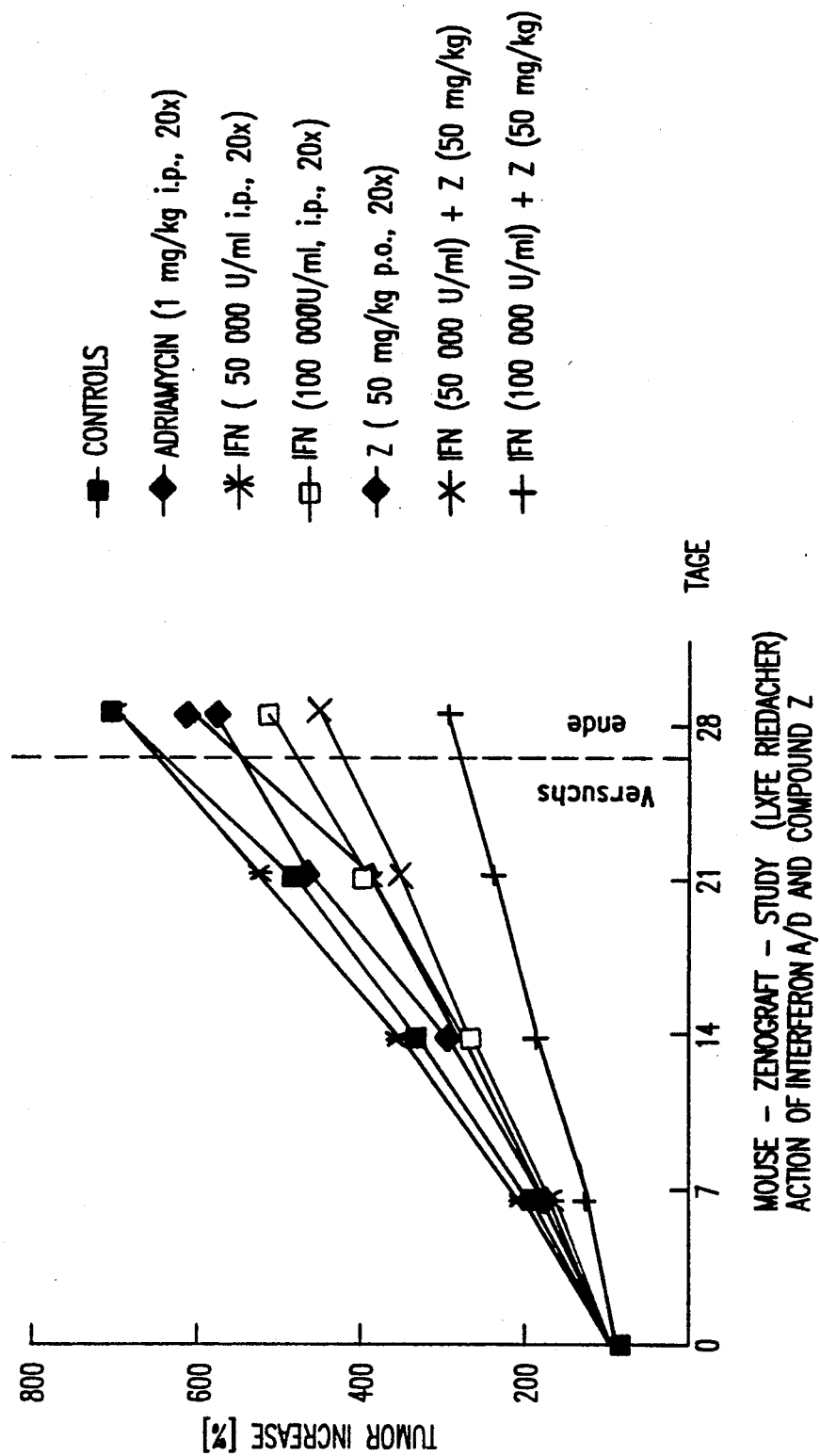

METHOD OF USING 4-(2-(P-((E)-2-(5,6,7,8-TETRAHYDRO-5,5,8,8-TETRAMETHYL-2-NAPHTHYL)PROPENYL)PHENOXY)ETHYL)MORPHOLINE WITH CYTOSTATICS

BRIEF SUMMARY OF THE INVENTION

The invention is concerned with the use of 4-[2-[p-[(E)-2-(5,6,7,8-tetrahydro-5,5,8,8-tetramethyl-2-naphthyl)propenyl]phenoxy]ethyl]-morpholine as an active substance for the manufacture of pharmaceutical preparations for supporting therapy with a cytostatic agent. In another aspect, the invention is concerned with a product containing 4-[2-[p-[(E)-2-(5,6,7,8-tetrahydro-5,5,8,8-tetramethyl-2-naphthyl)propenyl]phenoxy]ethyl]morpholine and a cytostatic agent as a combination preparation for the simultaneous, separate or sequential use in cancer prophylaxis or therapy particularly for cancers which are sensitive to such a combination. The invention is also concerned with a commercial pack containing as the pharmaceutically active substance 4-[2-[p-[(E)-2-(5,6,7,8-tetrahydro-5,5,8,8-tetramethyl-2-naphthyl)propenyl]phenoxy]ethyl]morpholine together with instructions for its use in combination with a cytostatic agent for the simultaneous, separate or sequential use in cancer prophylaxis or therapy particularly for cancers which are sensitive to such a combination. The invention is also concerned with a method of cancer prophylaxis or therapy in mammals which comprises administering 4-[2-[p-[(E)-2-(5,6,7,8-tetrahydro-5,5,8,8-tetramethyl-2-naphthyl)propenyl]phenoxy]ethyl]morpholine simultaneously, separately or a sequentially in combination with a cytostatic agent particularly for cancers which are sensitive to such a combination.

Therapy with cytostatic agents is frequently associated with undesirable effects which have their origin in the toxicity of the cytostatic agent. Examples of such undesirable effects are hair loss, weight loss or inappetence, bone marrow disorders, gastrointestinal disorders, myocardial changes, testicular changes, liver and kidney disorders.

It has now been found that these undesirable effects during therapy with cytostatic agents can be reduced or avoided when the compound 4-[2-[p-[(E)-2-(5,6,7,8-tetrahydro-5,5,8,8-tetra-methyl-2-naphthyl)propenyl]-phenoxy]ethyl]morpholine (referred to hereinafter as "Compound Z") is administered simultaneously or sequentially.

DETAILED DESCRIPTION OF THE INVENTION

Accordingly, the invention is concerned with the use of 4-[2-[p-[(E)-2-(5,6,7,8-tetrahydro-5,5,8,8-tetramethyl-2-naphthyl)propenyl]phenoxy]ethyl]-morpholine as an active substance for the manufacture of pharmaceutical preparations for supporting therapy with a cytostatic agent. In another aspect, the invention is concerned with a product containing 4-[2-[p-[(E)-2-(5,6,7,8-tetrahydro-5,5,8,8-tetramethyl-2-naphthyl)propenyl]phenoxy]-ethyl]morpholine and a cytostatic agent as a combination preparation for the simultaneous, separate or sequential use in cancer prophylaxis or therapy particularly for cancers which are sensitive to such a combination. In another aspect, the invention is also concerned with a commercial pack containing as the pharmaceutically active substance 4-[2-[p-[(E)-2-(5,6,7,8-tetrahydro-5,5,8,8-tetramethyl-2-napthyl)propenyl]-phenoxy]ethyl]morpholine together with instructions for its use in combination with a cytostatic agent for the simultaneous, separate or sequential use in cancer prophylaxis or therapy particularly for cancers which are sensitive to such a combination. In still another aspect, the invention is concerned with a method of cancer prophylaxis or therapy in mammals which comprises administering 4-[2-[p-(E)-2-(5,6,7,8-tetrahydro-5,5,8,8-tetramethyl-2-naphthyl)propenyl]phenoxy]ethyl]morpholine simultaneously, separately or a sequentially in combination with a cytostatic agent particularly for cancers which are sensitive to such a combination.

Compound Z, its manufacture and use as a medicament, for example, in the therapy of cancer, is described in European Patent Publication A-2 0 331 983.

Cytostatic agents whose undesirable effects can be reduced or avoided by simultaneous or sequential therapy with Compound Z are those of teh alkylating substance type such as, for example, cyclo-phosphamide; platinum derivatives; antimetabolites, for example, folic acid analogues such as methotrexate, or pyrimidine derivatives such as 5-fluororacil; anthracyclines such as doxorubicin; vinca alkaloids such as vinblastin or vincristin; as well as "Biological Response Modifiers" (BRM) such as interleukins, for example, IL-2 and interferons, for example, IFNα and IFNγ, Colony Stimulating Factors, for example, G-CSF, GM-CSF and M-CSF, and retinoids, for example, temarotene. The reduction of the undesired effects is achieved by the fact that the substances described above can be administered in lower dosages in combination with Compound Z without reducing their antitumor activity.

Furthermore, it has been found that the simultaneous administration of Compound Z and interleukin or doxorubicin inhibits the tumor growth of tumors which are sensitive to such a combination to a greater than an additive inhibitory effect. In combination with cyclophosphamide (CY), the toxicity of CY was largely offset.

The undesirable effects during tumor treatment with Compound Z and other cytostatic is documentated by the following test results:

A. Treatment of Chemically-Induced Mammary Tumors in Rats With Cyclophosphamide and Compound Z Female rats aged 50 days were given a single oral dosage of 12 mg of 7,12-dimethylbenz(a)anthracene in 0.5 ml of arachis oil. After about 8 weeks, the rats which had developed mammary tumors were divided into groups of 10. One group was given only feed without the addition of test substance; one group was given 75 mg/kg/day (7 times weekly) of Compound Z as a feed additive; one group was given 10 mg/kg/day of cyclophosphamide intra-peritoneally (5 times weekly); one group was given Compound Z and cyclophosphamide in the indicated dosages. The treatment extended over 10 weeks. Thereafter, the number of tumors, tumor volumes and mortality were determined. The results are set forth in Table 1 and FIGS. 1-3.

TABLE 1

| Group | Compound(s) | Tumor incidence in the group [%] | Average number of tumors/rat | Average tumour burden [cm³] | Number of surviving rats | Body weight [g] |
| --- | --- | --- | --- | --- | --- | --- |
| Start of test | | | | | | |
| 1 | Control | 100 | 2.8 ± 0.5 | 2.8 | 10 | 251 ± 5 |
| 2 | Z | 100 | 3.1 ± 0.5 | 4.0 | 10 | 256 ± 4 |
| 3 | Cy | 100 | 2.4 ± 0.4 | 2.6 | 10 | 266 ± 6 |
| 4 | Cy + Z | 100 | 2.7 ± 0.4 | 3.2 | 10 | 252 ± 5 |
| After 6 weeks | | | | | | |
| 1 | Control | 100 | 6.0 ± 0.8 | 100.2 | 10 | 267 ± 10 |
| 2 | Z | 100 | 4.0 ± 0.6 | 9.6 | 9 | 246 ± 6 |
| 3 | Cy | 100 | 5.7 ± 0.5 | 10.3 | 10 | 249 ± 5 |
| 4 | Cy + Z | 80 | 1.7 ± 0.4 | 1.5 | 10 | 243 ± 5 |
| After 10 weeks | | | | | | |
| 1 | Control | 100 | 6.6 ± 0.8 | 119.5 | 9 | 285 ± 8 |
| 2 | Z | 100 | 3.4 ± 0.6 | 10.9 | 9 | 255 ± 6 |
| 3 | Cy | NU | NU | NU | 0 | NU |
| 4 | Cy + Z | 80 | 2.8 ± 0.8 | 3.6 | 10 | 253 ± 5 |

NU = not used

The data obtained show the tumor-inhibiting effect of the two test compounds, which appears to be additive in the case of combined administration. It surprisingly emerged that all experimental animals which had been given cyclophosphamide and Compound Z survived the entire test duration, while the unaccompanied administration of cyclophosphamide led to the premature death of all experimental animals.

Figure 1:
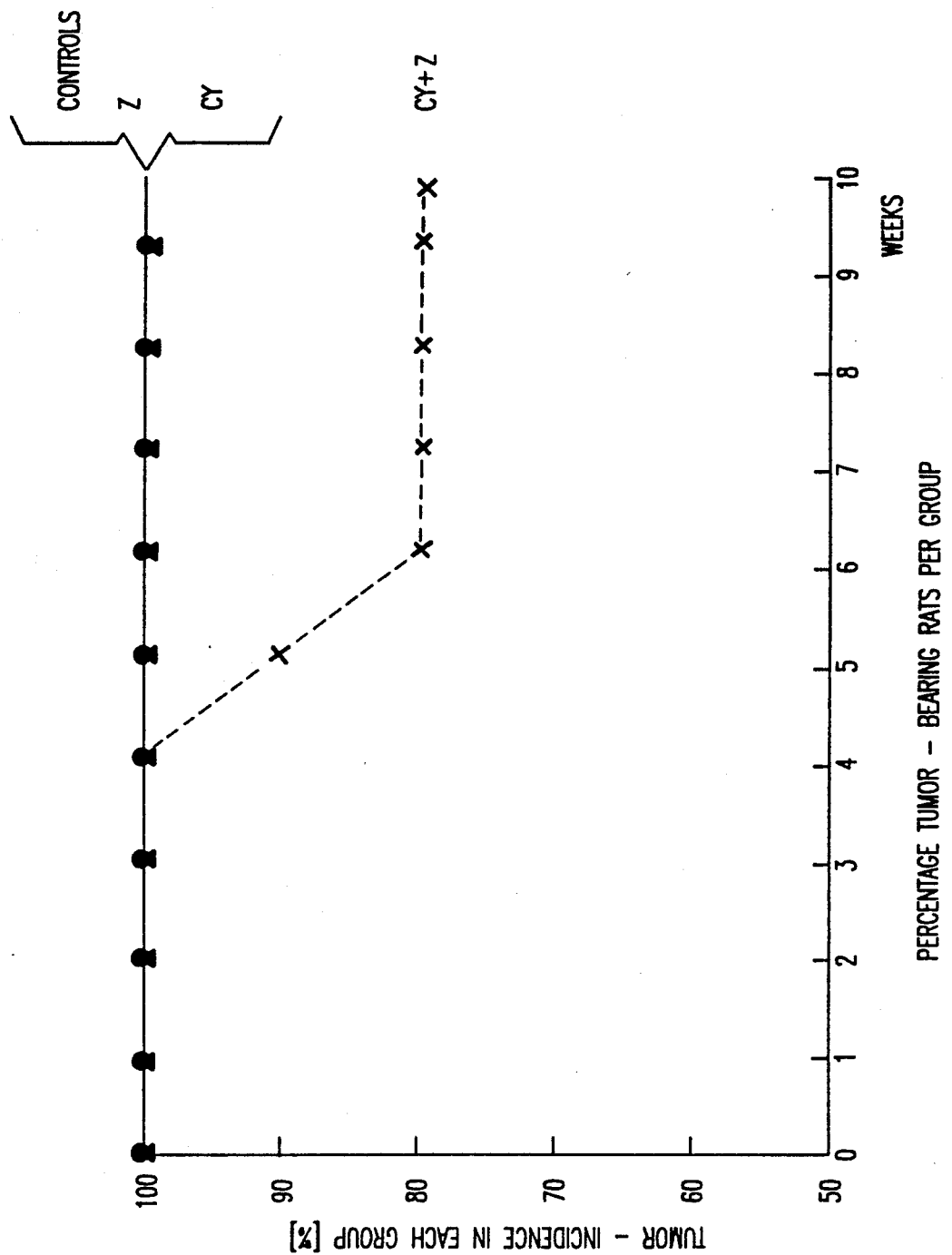
FIG. 1 shows the tumor incidence expressed as the percentage of the tumor-bearing rats of a group.
Figure 2:
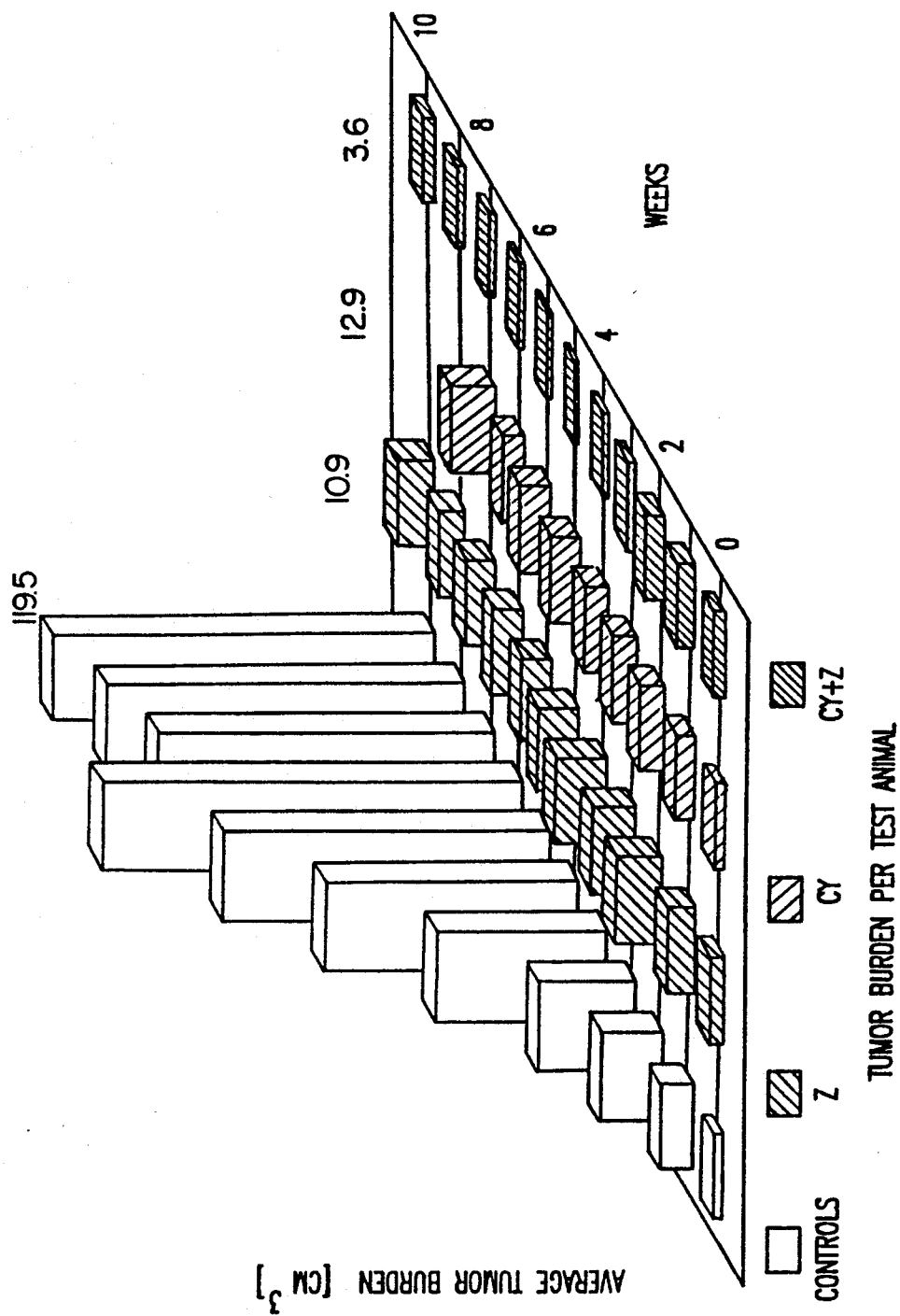
FIG. 2 shows the average tumor burden per animal, which is the product of the average number of tumors and the average tumor volume per rat.
Figure 3:
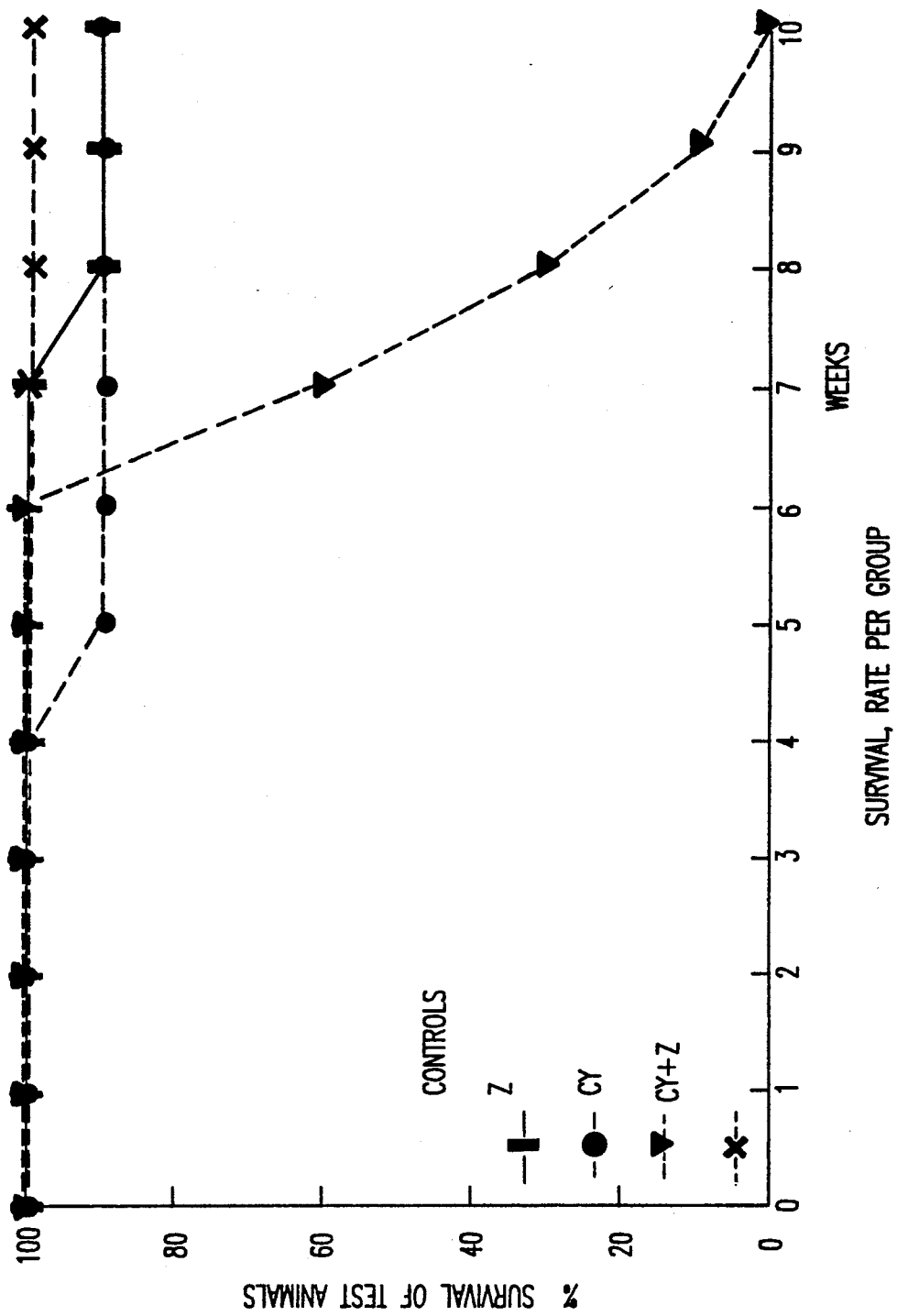

FIG. 3 shows the survival rate of the test animals. All animals which were treated with the combination of Z and cyclophosphamide survived to the end of the test, whereas in the cyclophosphamide-treated group all animals died prematurely with symptoms of anaemia, weakness and weight loss. These data shows that Compound Z clearly reduces the toxicity of cyclophosphamide.

B. Treatment of Chemically-Induced Mammary Tumors in Rats with Interleukin-2 and Compound Z.

Female rats with mammary tumors induced as described under A were given 75 mg/kg/day of Compound Z orally as a feed additive; or 1μ/kg/day of interleukin-2 i.p., 5 times weekly; or both test compounds. The duration of the treatment was 10 weeks. The dosage of IL-2 is an exceptionally low dosage which is very well tolerated. The results are given in Table 2 and FIGS. 4 and 5:

TABLE 2

| Group | Compound(s) | Tumor incidence in the group [%] | Average number of tumors/rat | Average tumor burden [cm³] | Surviving rats [%] | Body weight [g] |
| --- | --- | --- | --- | --- | --- | --- |
| Start of test | | | | | | |
| 1 | Control | 100 | 3.0 ± 2.0 | 3.6 ± 2.1 | 100 | 287 ± 26 |
| 2 | Z | 100 | 2.7 ± 0.6 | 6.0 ± 5.0 | 100 | 275 ± 4 |
| 3 | IL-2 | 100 | 2.8 ± 0.7 | 3.4 ± 1.2 | 100 | 285 ± 10 |
| 4 | IL-2 + Z | 100 | 2.5 ± 0.6 | 4.0 ± 2.7 | 100 | 293 ± 9 |
| After 6 weeks | | | | | | |
| 1 | Control | 100 | 4.0 ± 2.0 | 17.7 ± 11.5 | 100 | 305 ± 30 |
| 2 | Z | 100 | 3.7 ± 1.0 | 14.2 ± 6.5 | 100 | 264 ± 6 |
| 3 | IL-2 | 100 | 3.0 ± 0.5 | 25.4 ± 13.4 | 100 | 296 ± 11 |
| 4 | IL-2 + Z | 83 | 1.5 ± 0.6 | 3.0 ± 2.3 | 100 | 265 ± 13 |
| After 10 weeks | | | | | | |
| 1 | Control | 100 | 5.5 ± 3.5 | 18.8 ± 12.4 | 100 | 320 ± 25 |
| 2 | Z | 100 | 3.3 ± 0.5 | 18.2 ± 12.1 | 100 | 261 ± 11 |
| 3 | IL-2 | 100 | 3.5 ± 0.6 | 33.9 ± 17.9 | 100 | 314 ± 13 |
| 4 | IL-2 + Z | 50 | 1.0 ± 0.6 | 2.6 ± 2.4 | 100 | 254 ± 9 |

Figure 4:
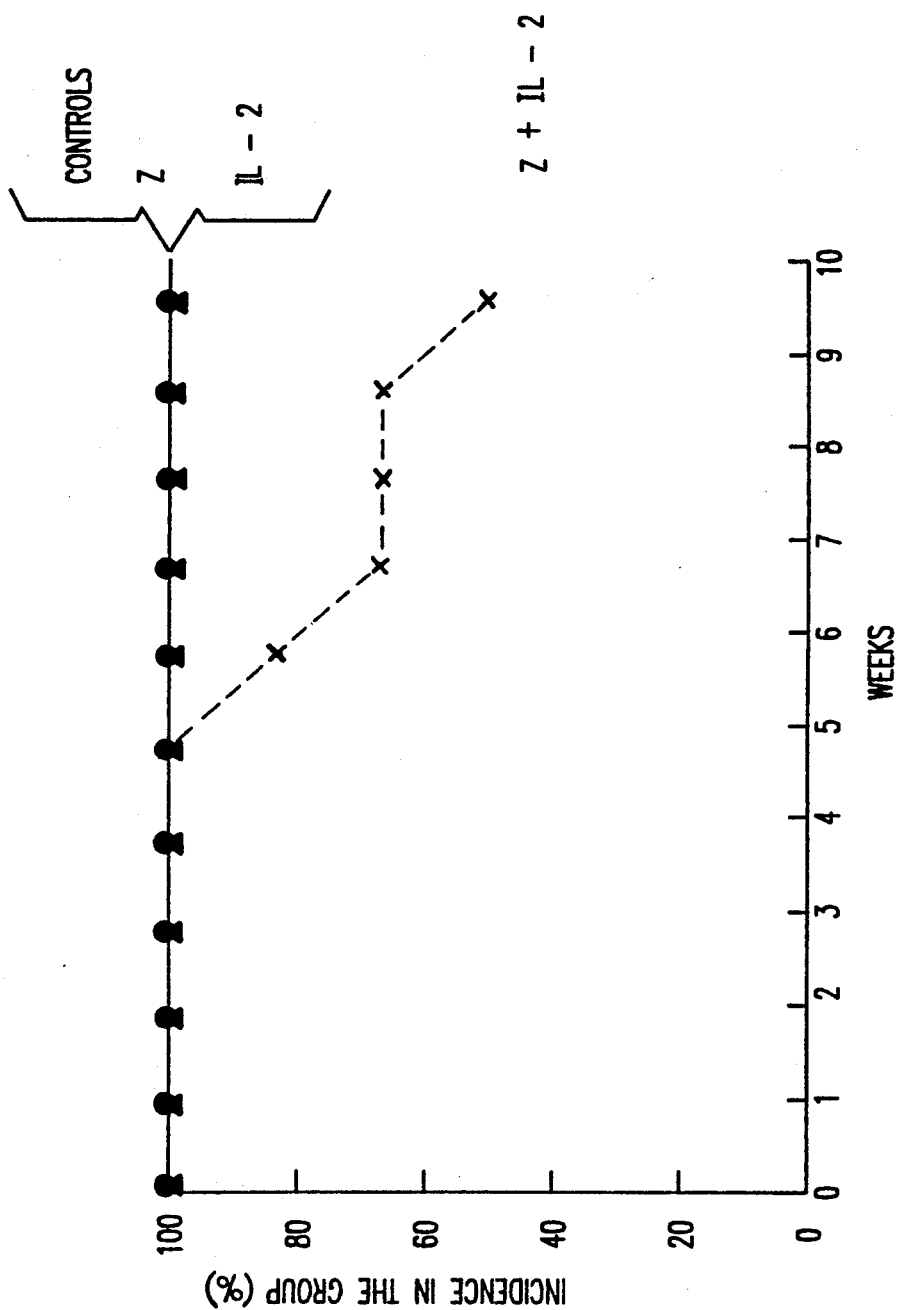

FIG. 4 shows that tumor incidence in the animals treated with Z or IL-2 remained unchanged compared with the control group. On the other hand, the combined treatment with Z and IL-2 led to the complete disappearance of the tumors in three out of six test animals.

Figure 5:
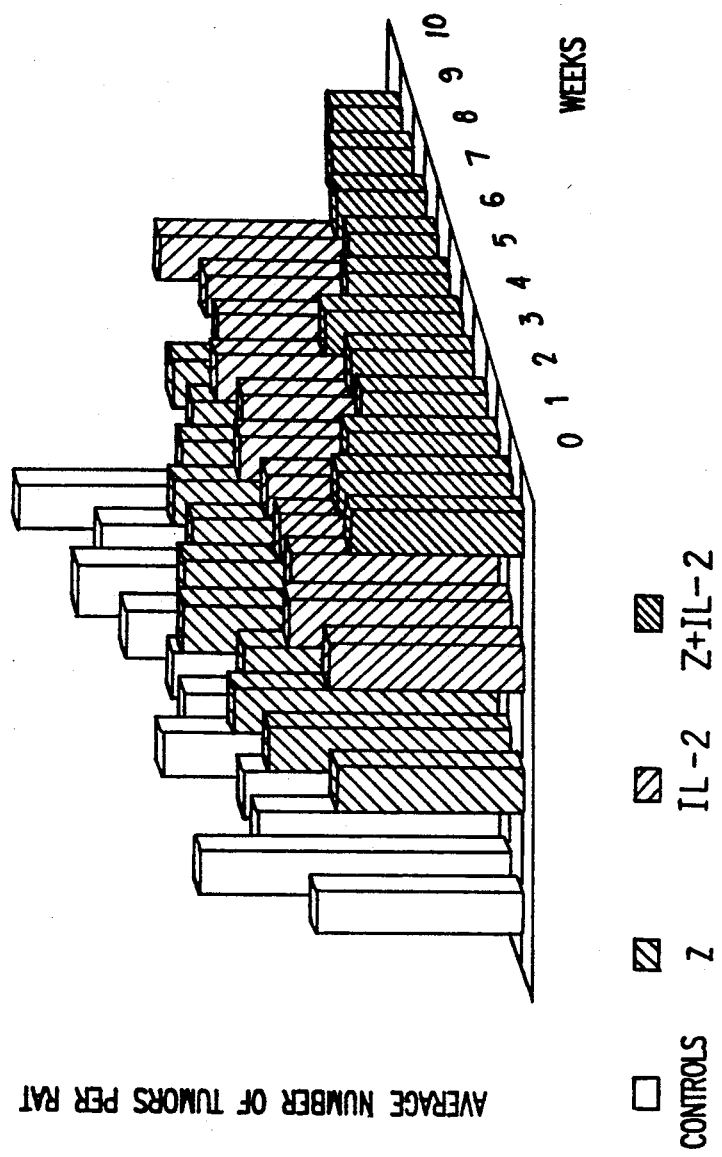

FIG. 5 shows the average number of tumors in the case of treatment with Z or IL-2, in the case of treatment with Z and IL-2 and without treatment (control group).

At the commencement of treatment the average tumor count was 3.4 per animal. This count doubled in the control group in the course of 10 weeks. The treatment with Z alone led to a reduction by 48% in the 5th week and thereafter to a slight increase by about 10%. The treatment with IL-2 alone had no effect on the number of tumors. In the combined treatment, the number of tumors had decreased by 67.5% after the 10th week.

C. Treatment of Chemically-Induced Mammary Tumors in Rats with Doxorubicin and Compound Z.

Female rats with mammary tumors induced as described under A were treated for 12 weeks with 75 mg/kg/day of Compound Z as a feed additive; or with 0.2 mg/kg of doxorubicin i.p. or with both test compounds. The treatment was effected 5 times weekly. The dosage of doxorubicin is an exceptionally low dosage with very good tolerance. The results are given in Table 3 and FIGS. 6–8.

TABLE 3

| Group | Compound(s) | Tumor incidence in the group [%] | Average number of tumors/rat | Average tumor burden [cm$^3$] | Number of surviving rats | Body weight [g] |
| --- | --- | --- | --- | --- | --- | --- |
| Start of test | | | | | | |
| 1 | Control | 100 | 5.2 ± 0.8 | 17.7 ± 6.4 | 7 | 290 ± 10 |
| 2 | Z | 100 | 5.7 ± 0.8 | 17.9 ± 6.4 | 7 | 306 ± 9 |
| 3 | Dox | 100 | 3.8 ± 0.7 | 11.8 ± 7.0 | 7 | 301 ± 16 |
| 4 | Dox + Z | 100 | 4.4 ± 6.0 | 15.0 ± 6.0 | 7 | 292 ± 15 |
| After 6 weeks | | | | | | |
| 1 | Control | 100 | 6.5 ± 1.0 | 96.2 ± 31.4 | 7 | 299 ± 14 |
| 2 | Z | 100 | 4.1 ± 0.9 | 14.1 ± 5.4 | 7 | 273 ± 6 |
| 3 | Dox | 100 | 4.2 ± 0.9 | 91.1 ± 54.4 | 7 | 301 ± 9 |
| 4 | Dox + Z | 71 | 2.5 ± 1.0 | 6.6 ± 5.7 | 7 | 254 ± 9 |
| After 12 weeks | | | | | | |
| 1 | Control | 100 | 6.4 ± 0.8 | 233.4 ± 105.3 | 100 | 318 ± 12 |
| 2 | Z | 100 | 4.4 ± 0.9 | 36.5 ± 22.2 | 100 | 275 ± 9 |
| 3 | Dox | 100 | 4.5 ± 0.7 | 197.8 ± 132.1 | 100 | 338 ± 28 |
| 4 | Dox + Z | 71 | 1.1 ± 0.4 | 1.2 ± 1.1 | 100 | 251 ± 9 |

Figure 6:
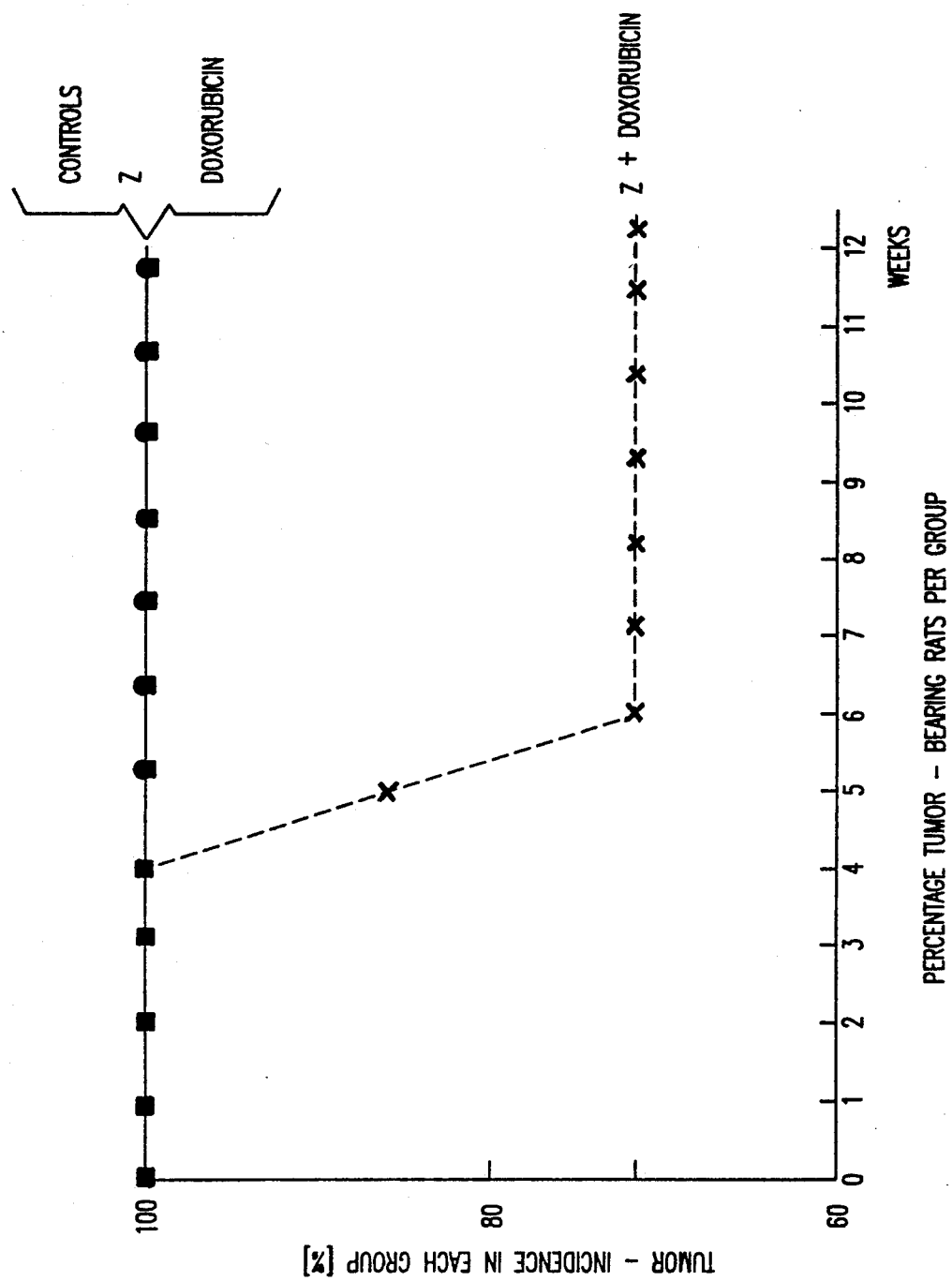

FIG. 6 shows tumor incidence expressed as the percentage of tumor-bearing animals in each group. The individual treatment with Z or doxorubicin showed no change here vis-a-vis the untreated control group.

Figure 7:
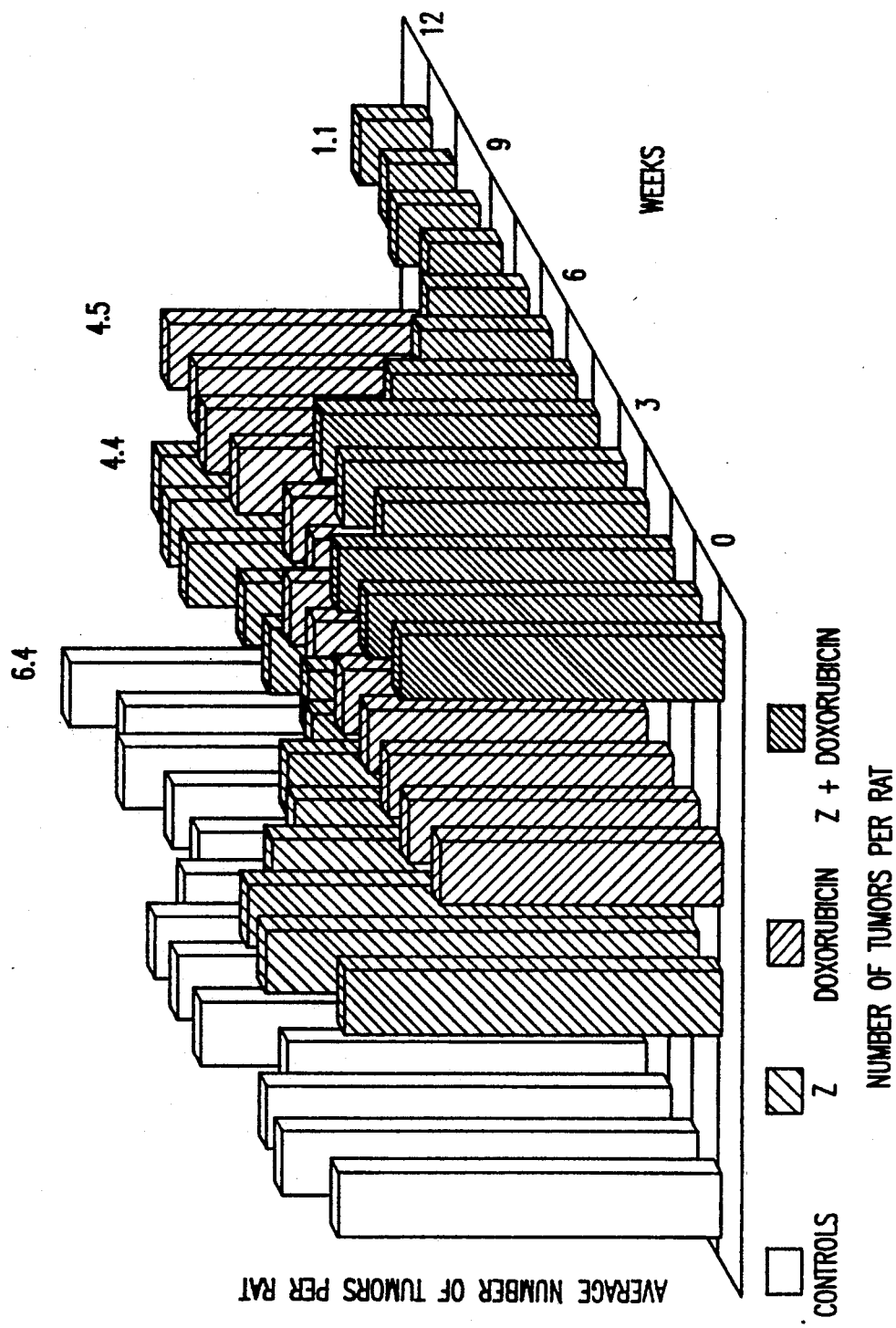
Figure 8:
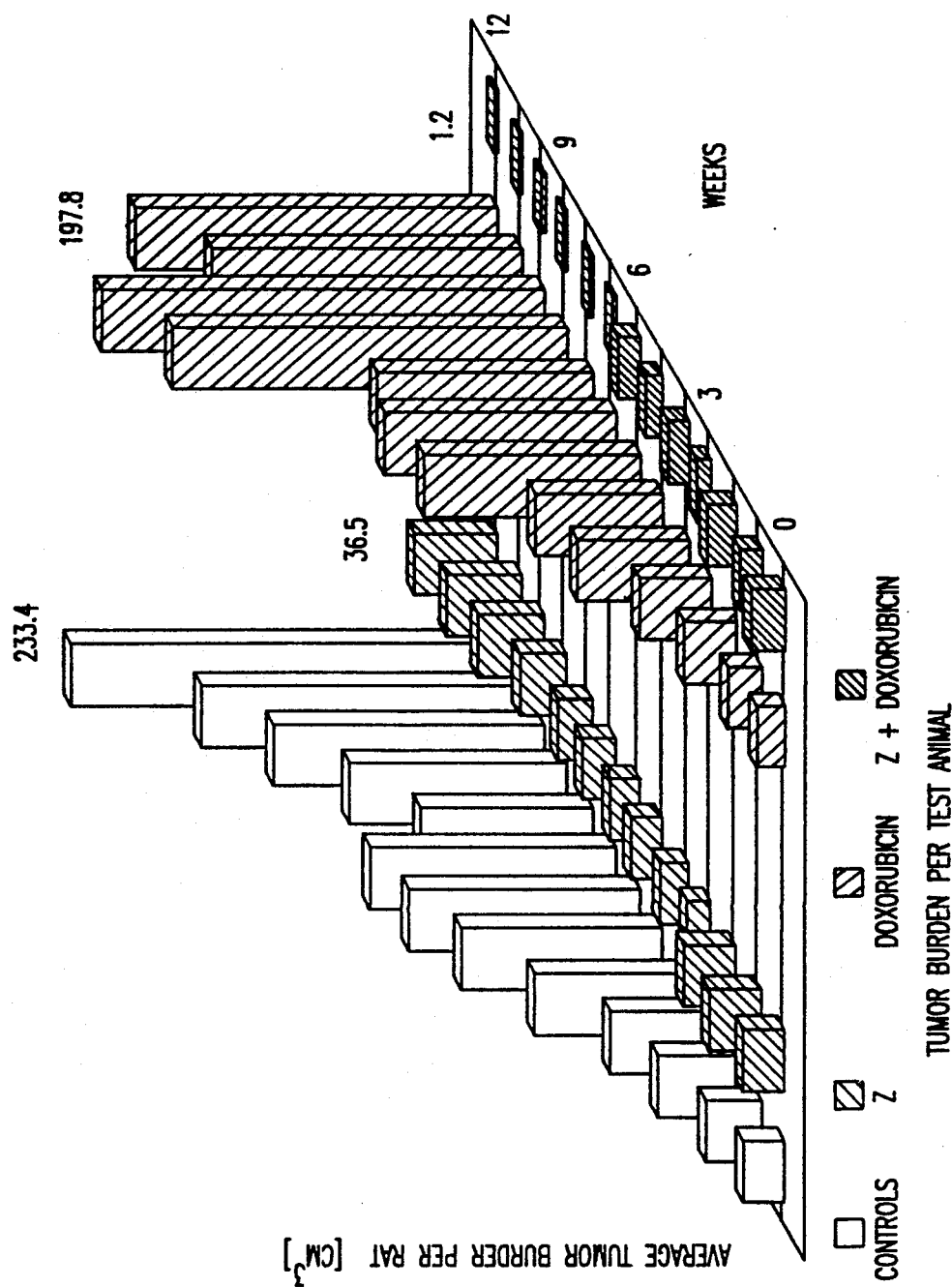

FIG. 7 shows that while the average number of tumors was reduced only slightly by treatment with the individual preparations, the combined administration showed a synergistic effect. A synergistic effect was also observed in the case of the parameter "average tumor burden per rat" (FIG. 8), which is the product of the average number of tumors and the average tumor volume.

D. Antiproliferative Activity of Compound Z in Combination with Interferon on Human Tumor Cells in Vitro Human mammary cell lines BT-20 (oestrogen receptor-negative) and ZR 75-1 (oestrogen receptor-positive) were used for this test. The cells were cultivated in RPMI 1640, which contained 10% FCS, and plated out on tissue culture plates. One day after the plating out, the cultures were treated with Compound Z and interferon individually and in combination for 14 days. Culture medium and test compounds were renewed every 2-3 days. Cell counts were undertaken at the beginning of the test at each change of the medium and at the end of the test. The interferons used were human hybrid rIFN-αAD, human interferon rIFNα2 (active ingredient of 'Roferon') and rIFNγ.

The results are presented in FIGS. 9–12. The results obtained with IFNαA/D and IFNα2 were the same, therefore only one curve is given for interferon.

Figure 9:
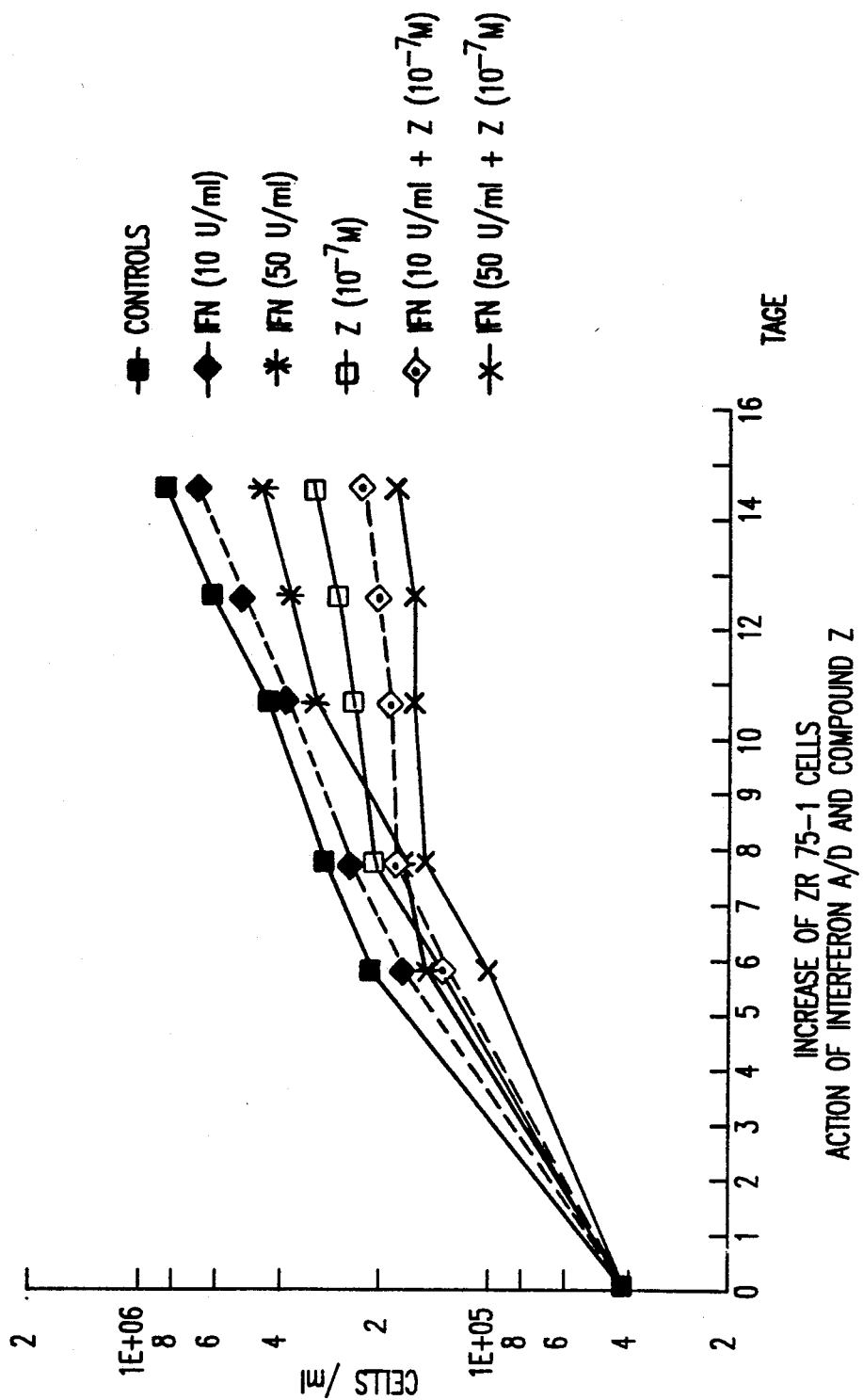

FIG. 9 shows that the concentration of 10 U/ml, which is almost inactive in the case of sole administration, clearly enhances the activity of Compound Z.

Figure 10:
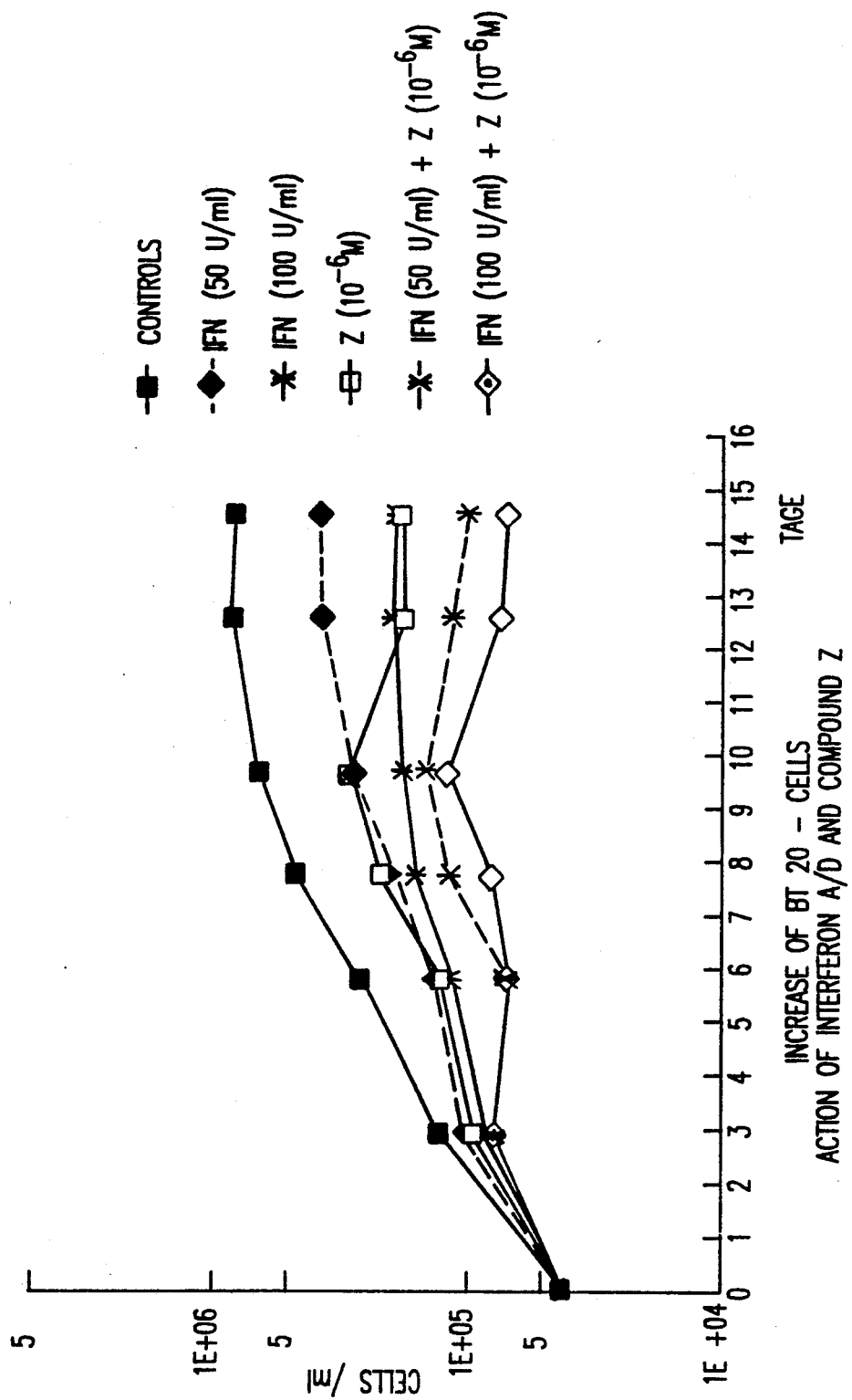

FIG. 10 shows that an almost complete inhibition of the cell proliferation was achieved with higher, but still non-toxic, dosages of the combination.

Figure 11:
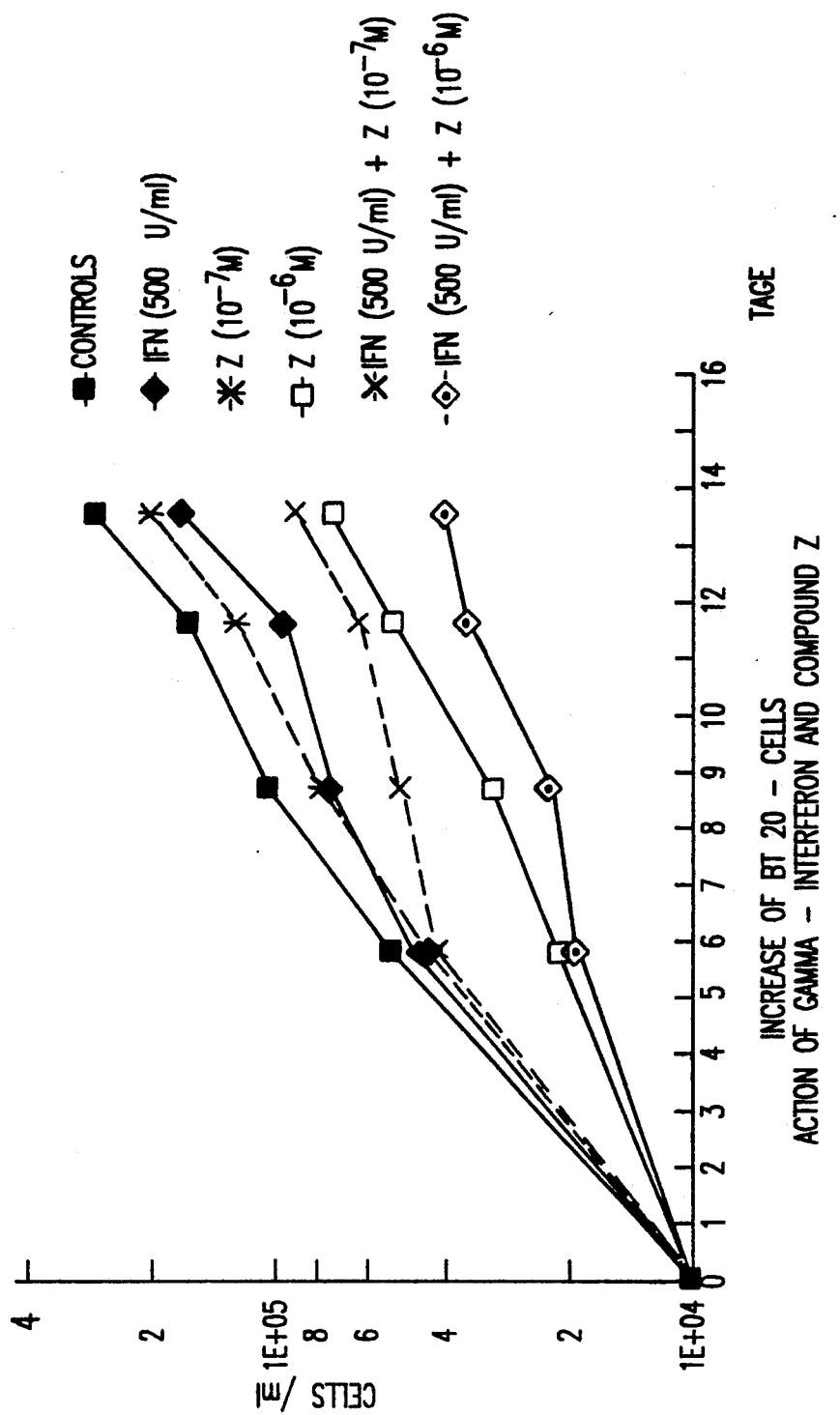

FIG. 11 shows that similar results were achieved with rIFNγ as with IFNαA/D.

Figure 12:
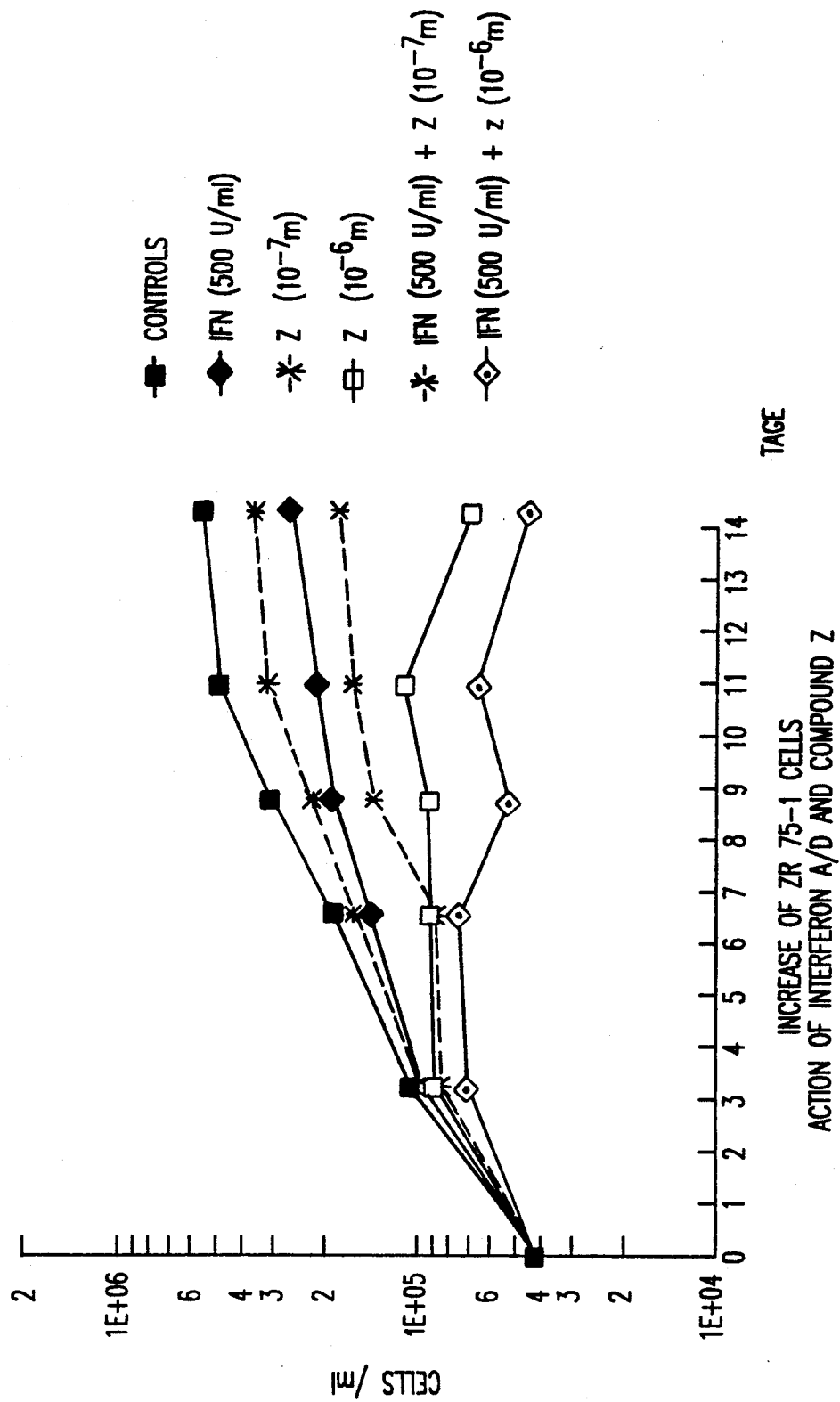

Also in the case of cell line ZR 75-1 the treatment with the combination of Compound Z and interferons led to a greater inhibition of the cell proliferation than the treatment with the individual components (FIG. 12 and 13).

Treatment of Human Bronchial Squamous Cell Carcinoma (Riedacher LXFE) in the Athymic Mouse About 1 mm$^3$ of tumor tissue was transplanted subcutaneously in the athymic mouse for this test. The treatment (50 mg/kg/day of arotinoid p.o.; 50,000 or 100,000 U/ml of interferon αA/D i.p., 5 times weekly for 4 weeks) was begun as soon as the transplants had grown to a diameter of about 0.5 cm. The tumor growth was determined weekly by measuring the size and small diameter of the tumors. Adriamycin (1 mg/kg/day i.p.) was used as the positive control.

The results are presented in FIG. 14. From this, it will be evident that the lower interferon dosage, which on its own had no influence on the tumor growth, clearly reduced the tumor growth in combination with compound Z.

In the use in accordance with the invention, Compound Z can be employed in the dosages and formulations which are known from European Patent Publication A2-0 331 983. The dosing in an individual case must be fitted to the requirements of the patient and to the other cytostatic or BRM used in parallel, which lies in the purview of the specialist knowledge.

I claim:

1. A method for cancer prophylaxis or therapy for mammary tumors in mammals which comprises administering to a mammal requiring such treatment an effective amount of 4-[2-[p-[(E)-2-(5,6,7,8-tetrahydro-5,5,8,8-tetramethyl-2-naphthyl)-propenyl]phenoxy]ethyl]-morpholine, simultaneously, separately or sequentially in combination with a synergistically effective amount of cyclophosphamide wherein the compounds are ratio of the amount of 4-[2-[p-[(E)-2-(5,6,7,8-tetrahydro-5,5,8,8-tetramethyl-2-naphthyl)propenyl]phenoxy]ethyl]-morpholine to the amount of cyclophosphamide is about 7.5 to 1.

2. A pharmaceutical composition containing an effective amount of 4-[2-[p-[(E)-2-(5,6,7,8-tetrahydro-5,5,8,8-tetramethyl-2-naphthyl)propenyl]phenoxy]ethyl]-morpholine, and a synergistically effective amount of cyclophosphamide wherein 4-[2-[p-[(E)-2-(5,6,7,8-tetrahydro-5,5,8,8-tetramethyl-2-naphthyl)propenyl]phenoxy]ethyl]-morpholine and cyclophosphamide are present in a ratio of about 7.5 to 1.

* * * * *